(12) United States Patent
Mannion et al.

(10) Patent No.: US 12,629,031 B2
(45) Date of Patent: May 19, 2026

(54) MINIMALLY INVASIVE DEVICE WITH SPECTROPHOTOMETER

(71) Applicant: ROCKLEY PHOTONICS LIMITED, Altrincham (GB)

(72) Inventors: Paul Mannion, Eliot, ME (US); Kate LeeAnn Bechtel, Pleasant Hill, CA (US); Suresh Chengalva, Carmel, IN (US); Chia-Te Chou, Brea, CA (US); Lok Man Chu, San Marino, CA (US); Craig Gardner, Belmont, MA (US); Alexander Gondarenko, San Jose, CA (US); Richard Grote, Rancho Cucamonga, CA (US); Vafa Jamali, Boulder, CO (US); Haydn Frederick Jones, London (GB); Jennifer Lynn Corso, Peoria, AZ (US); Roozbeh Parsa, Portola Valley, CA (US); Kyle Rick, Boulder, CO (US); Aaron John Zilkie, Pasadena, CA (US)

(73) Assignee: Rockley Photonics Limited, Altrincham (GB)

( * ) Notice: Subject to any disclaimer, the term of this patent is extended or adjusted under 35 U.S.C. 154(b) by 529 days.

(21) Appl. No.: 18/266,789

(22) PCT Filed: Dec. 13, 2021

(86) PCT No.: PCT/IB2021/000895
§ 371 (c)(1),
(2) Date: Jun. 12, 2023

(87) PCT Pub. No.: WO2022/130022
PCT Pub. Date: Jun. 23, 2022

(65) Prior Publication Data
US 2024/0041328 A1 Feb. 8, 2024

Related U.S. Application Data

(60) Provisional application No. 63/125,254, filed on Dec. 14, 2020.

(51) Int. Cl.
*A61B 5/00* (2006.01)
*A61B 1/00* (2006.01)
(Continued)

(52) U.S. Cl.
CPC ........ *A61B 5/0075* (2013.01); *A61B 1/00165* (2013.01); *A61B 1/012* (2013.01);
(Continued)

(58) Field of Classification Search
CPC ..... A61B 1/00165; A61B 1/012; A61B 1/018; A61B 1/07; A61B 5/0066; A61B 5/0075;
(Continued)

(56) References Cited

U.S. PATENT DOCUMENTS 5,807,261 A * 9/1998 Benaron .............. A61B 5/0086
600/476
2011/0218445 A1 9/2011 Braun et al.
(Continued)

FOREIGN PATENT DOCUMENTS

WO WO 98/39807 A1 9/1998

OTHER PUBLICATIONS

Hakala, et al. "Sampling of Fluid Through Skin with Magnetohydrodynamics for Noninvasive Glucose Monitoring," Nature Scientific Reports, 2021, 11: 7609, 9 pages.
(Continued)

*Primary Examiner* — Mark R Gaworecki
(74) *Attorney, Agent, or Firm* — Womble Bond Dickinson (US) LLP

(57) ABSTRACT
A minimally invasive spectrophotometric system. In some embodiments, the system includes a minimally invasive
(Continued)

device and a spectrophotometer. The spectrophotometer may include: a transmitting fiber, a receiving fiber, and a head. The head of the spectrophotometer may include: a light source connected to the transmitting fiber and a photodetector connected to the receiving fiber. A portion of the transmitting fiber may be in an insertion tube of the minimally invasive device, and a portion of the receiving fiber may be in the insertion tube of the minimally invasive device. The head of the spectrophotometer may occupy a volume of less than 300 cubic centimeters.

19 Claims, 14 Drawing Sheets

(51) Int. Cl.

| | |
|---|---|
| *A61B 1/01* | (2006.01) |
| *A61B 1/012* | (2006.01) |
| *A61B 1/07* | (2006.01) |
| *A61B 10/02* | (2006.01) |
| *A61B 10/04* | (2006.01) |
| *A61B 1/018* | (2006.01) |
| *A61B 10/06* | (2006.01) |

(52) U.S. Cl.
CPC .............. *A61B 1/07* (2013.01); *A61B 5/6833* (2013.01); *A61B 5/6848* (2013.01); *A61B 5/6852* (2013.01); *A61B 10/0233* (2013.01); *A61B 10/04* (2013.01); *A61B 1/018* (2013.01); *A61B 5/0066* (2013.01); *A61B 5/0084* (2013.01); *A61B 2010/045* (2013.01); *A61B 10/06* (2013.01); *A61B 2562/0238* (2013.01); *A61B 2562/185* (2013.01)

(58) Field of Classification Search
CPC ... A61B 5/0084; A61B 5/6833; A61B 5/6848; A61B 5/6852; A61B 10/0233; A61B 10/04; A61B 10/06; A61B 2010/045; A61B 2562/0238; A61B 2562/185
See application file for complete search history.

(56) References Cited

U.S. PATENT DOCUMENTS

| | | | |
|---|---|---|---|
| 2012/0184827 | A1 | 7/2012 | Schwartz et al. |
| 2015/0265256 | A1 | 9/2015 | Bierhoff et al. |
| 2017/0173275 | A1 | 6/2017 | Anderson et al. |
| 2020/0069225 | A1 | 3/2020 | Vizbara et al. |

OTHER PUBLICATIONS

International Search Report for PCT/IB2021/000895 dated Jun. 1, 2022, 4 pages.
International Search Report and Written Opinion of the International Searching Authority, mailed Jun. 1, 2022, corresponding to PCT/IB2021/000895, 20 pages.

* cited by examiner

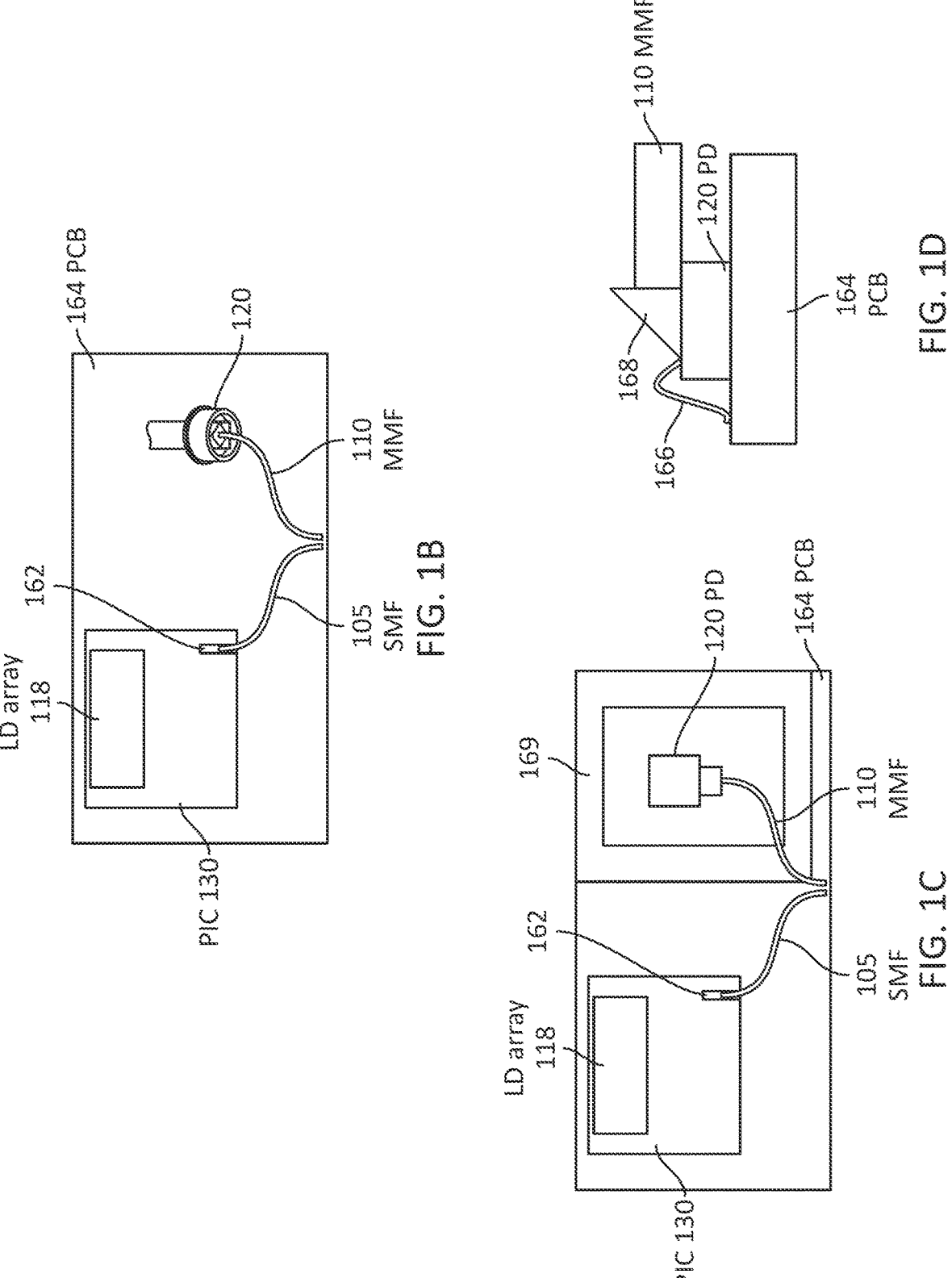

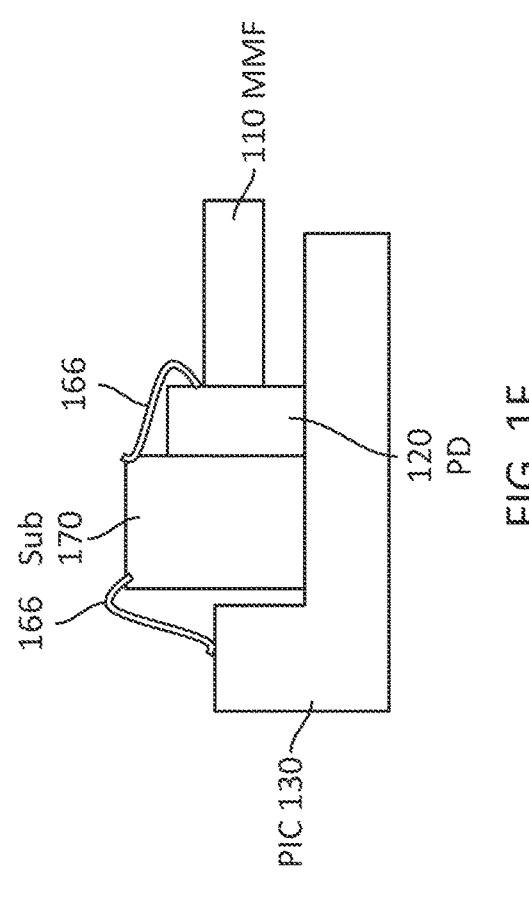
FIG. 1F
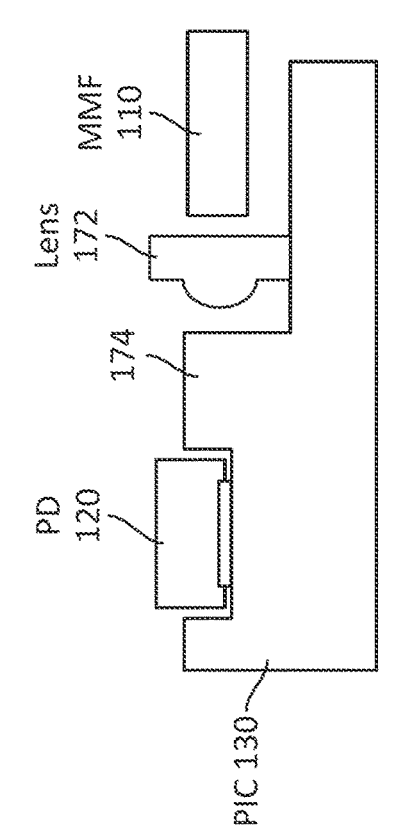
FIG. 1H
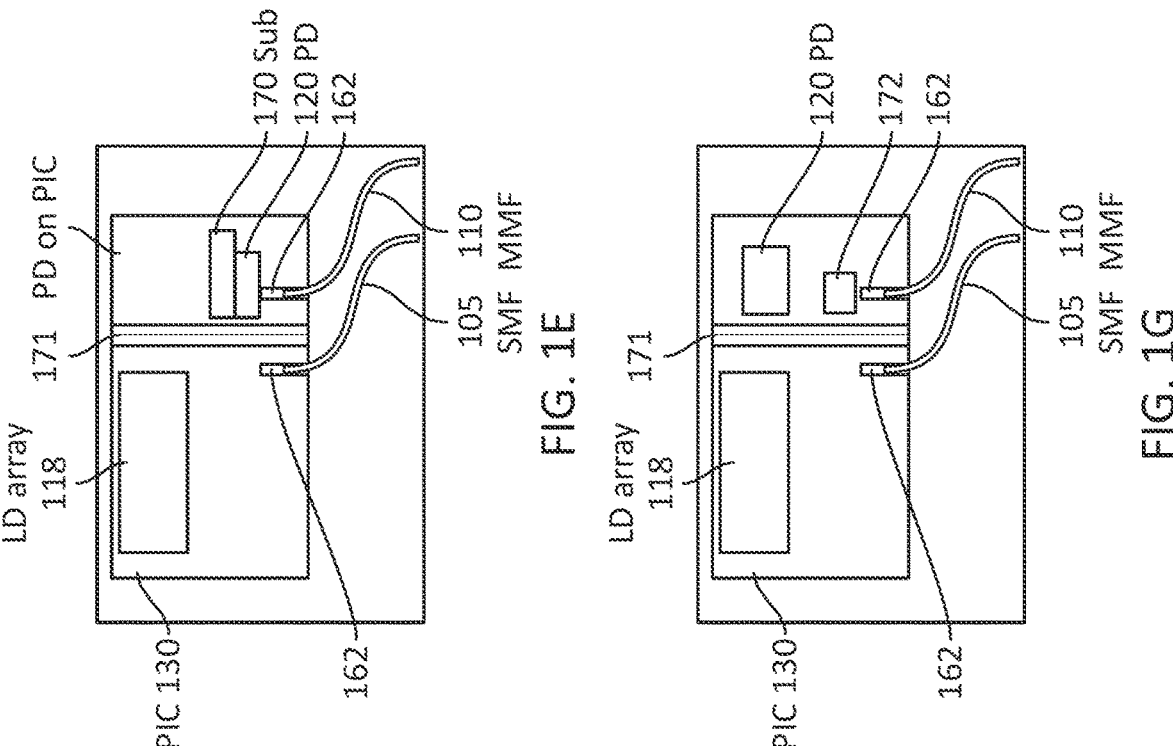
FIG. 1E
FIG. 1G

MINIMALLY INVASIVE DEVICE WITH SPECTROPHOTOMETER

CROSS-REFERENCE TO RELATED APPLICATIONS

The present application is a U.S. National Phase Patent Application of International Application No. PCT/IB2021/000895, filed on Dec. 13, 2021, which claims priority to and the benefit of U.S. Provisional Application No. 63/125,254, filed Dec. 14, 2020, the entire content of each of which is incorporated herein by reference.

FIELD

One or more aspects of embodiments according to the present disclosure relate to optical sensing, and more particularly to minimally invasive spectrophotometric sensing.

BACKGROUND

In various clinical or home health care settings, obtaining spectrophotometric data from tissue of a subject may be advantageous, e.g., to sense levels of chemical compounds (e.g., glucose) in the tissue, to measure other characteristics (e.g., the temperature) of the tissue, or to distinguish different kinds of tissue (e.g., to distinguish healthy tissue from diseased tissue).

Thus, there is a need for a system and method for obtaining spectrophotometric data.

SUMMARY

According to an embodiment of the present disclosure, there is provided a system including: a minimally invasive device; and a spectrophotometer, the spectrophotometer including: a transmitting fiber; a receiving fiber; and a head, the head of the spectrophotometer including: a light source connected to the transmitting fiber; and a photodetector connected to the receiving fiber, wherein: a portion of the transmitting fiber is in an insertion tube of the minimally invasive device; a portion of the receiving fiber is in the insertion tube of the minimally invasive device; and the head of the spectrophotometer occupies a volume of less than 300 cubic centimeters.

In some embodiments, the spectrophotometer is a single-use device.

In some embodiments, the minimally invasive device is a single-use device, and the spectrophotometer is integrated into the minimally invasive device.

In some embodiments, the head of the spectrophotometer includes: a plurality of lasers, each configured to operate within a different respective wavelength range, and a multiplexer, having a plurality of inputs and an output, for combining the outputs of the lasers, wherein the transmitting fiber is connected to the output of the multiplexer.

In some embodiments, the head of the spectrophotometer includes a photonic integrated circuit including the multiplexer, wherein the plurality of lasers is mounted on the photonic integrated circuit and each of the lasers is coupled into a waveguide on the photonic integrated circuit.

In some embodiments, a proximal end of the transmitting fiber is secured in a V-groove on the photonic integrated circuit.

In some embodiments, the photodetector is in a TO can, and the receiving fiber is coupled into the TO can.

In some embodiments, the photodetector includes a bare photodetector die mounted on a printed circuit board, and the receiving fiber is coupled to the photodetector die through a prism.

In some embodiments: the photodetector is mounted on a ceramic substrate, the photodetector and the ceramic substrate are mounted on the photonic integrated circuit, the photodetector is perpendicular to the photonic integrated circuit, and the receiving fiber is secured in a V-groove in the photonic integrated circuit.

In some embodiments: the photodetector is mounted on the photonic integrated circuit and edge-coupled to a waveguide on the photonic integrated circuit, and the receiving fiber is secured in a V-groove in the photonic integrated circuit, and coupled to the waveguide.

In some embodiments, the multiplexer is an arrayed waveguide grating, an echelle grating, or a cascaded Mach-Zehnder multiplexer.

In some embodiments, the spectrophotometer is configured to perform coherent detection of light received via the receiving fiber.

In some embodiments, the spectrophotometer is configured to perform direct detection of light received via the receiving fiber.

In some embodiments, the head of the spectrophotometer includes an enclosure or one or more baffles for providing optical isolation between the photodetector and the light source.

In some embodiments, the head of the spectrophotometer includes a battery and a wireless communication interface.

In some embodiments, the head of the spectrophotometer occupies a volume of less than 10 cubic centimeters.

In some embodiments, the receiving fiber is a first receiving fiber, and the spectrophotometer further includes a second receiving fiber.

In some embodiments, the receiving fiber is a multimode fiber.

In some embodiments: the minimally invasive device is wearable device: the insertion tube is a hollow needle configured to penetrate the surface of the skin of a subject, the wearable device includes a housing, the head of the spectrophotometer is in the housing, and the hollow needle is secured to the housing.

In some embodiments, the housing is configured to be secured to the skin of the subject with an adhesive sheet.

In some embodiments, the minimally invasive device further includes an actuator for vibrating the hollow needle.

In some embodiments: the minimally invasive device is a biopsy needle, the insertion tube is a percutaneous needle of the biopsy needle, and the biopsy needle includes a handle.

In some embodiments, the head of the spectrophotometer is in the handle.

In some embodiments, the transmitting fiber and the receiving fiber are configured to be retracted to vacate a volume, for holding a biopsy sample, at the tip of the percutaneous needle.

In some embodiments, the head of the spectrophotometer is configured to slide within the handle to advance or retract the transmitting fiber and the receiving fiber within the percutaneous needle.

In some embodiments, each of the transmitting fiber and the receiving fiber has a bend within the handle, the bend being configured to include varying amounts of fiber and to enable the transmitting fiber and the receiving fiber to be advanced or retracted within the percutaneous needle.

In some embodiments, a portion of the transmitting fiber or a portion of the receiving fiber is embedded within the wall of the percutaneous needle.

In some embodiments: the minimally invasive device is an endoscope, the insertion tube is a shaft of the endoscope, and the endoscope includes a handle.

In some embodiments, the head of the spectrophotometer is in the handle. In some embodiments, a portion of the transmitting fiber or a portion of the receiving fiber is embedded within the wall of the shaft of the endoscope.

In some embodiments, the minimally invasive device further includes a treatment laser fiber, and a portion of the transmitting fiber or a portion of the receiving fiber is contained, with the treatment laser fiber, in a sheath.

According to an embodiment of the present disclosure, there is provided a method, including: obtaining spectrophotometric data from a subject with a system including a minimally invasive device and a spectrophotometer.

In some embodiments, the method further includes calibrating another sensor, on the subject, based on the spectrophotometric data.

In some embodiments, the method further includes calibrating the spectrophotometer based on another sensor on the subject.

In some embodiments, the method further includes: applying energy to a tissue of the subject, and estimating the temperature of the tissue based on the spectrophotometric data.

In some embodiments, the method further includes performing laser lithotripsy in a kidney of the subject, wherein the estimating of the temperature of the tissue includes estimating the temperature of kidney tissue of the subject.

In some embodiments, the estimating of the temperature includes estimating the center wavelength of an absorption peak of water.

According to an embodiment of the present disclosure, there is provided a system including: a minimally invasive device; and a spectrophotometer, the spectrophotometer including: a light source; and a photodetector, wherein: the spectrophotometer is in a channel of an insertion tube of the minimally invasive device, or the spectrophotometer is configured to be optically coupled to tissue of a subject through a channel of an insertion tube of the minimally invasive device.

In some embodiments, the spectrophotometer is a single-use device.

In some embodiments, the minimally invasive device is a single-use device, and the spectrophotometer is integrated into the minimally invasive device.

In some embodiments, the head of the spectrophotometer includes: a plurality of lasers, each configured to operate within a different respective wavelength range, and a multiplexer, having a plurality of inputs and an output, for combining the outputs of the lasers, wherein the transmitting fiber is connected to the output of the multiplexer.

In some embodiments, the head of the spectrophotometer includes a photonic integrated circuit including the multiplexer, wherein the plurality of lasers is mounted on the photonic integrated circuit and each of the lasers is coupled into a waveguide on the photonic integrated circuit.

In some embodiments, a proximal end of the transmitting fiber is secured in a V-groove on the photonic integrated circuit.

In some embodiments, the photodetector is in a TO can, and the receiving fiber is coupled into the TO can.

In some embodiments, the photodetector includes a bare photodetector die mounted on a printed circuit board, and the receiving fiber is coupled to the photodetector die through a prism.

In some embodiments: the photodetector is mounted on a ceramic substrate, the photodetector and the ceramic substrate are mounted on the photonic integrated circuit, the photodetector is perpendicular to the photonic integrated circuit, and the receiving fiber is secured in a V-groove in the photonic integrated circuit.

In some embodiments: the photodetector is mounted on the photonic integrated circuit and edge-coupled to a waveguide on the photonic integrated circuit, and the receiving fiber is secured in a V-groove in the photonic integrated circuit, and coupled to the waveguide.

In some embodiments, the multiplexer is an arrayed waveguide grating, an echelle grating, or a cascaded Mach-Zehnder multiplexer.

In some embodiments, the spectrophotometer is configured to perform coherent detection of light received via the receiving fiber.

In some embodiments, the spectrophotometer is configured to perform direct detection of light received via the receiving fiber.

In some embodiments, the head of the spectrophotometer includes an enclosure or one or more baffles for providing optical isolation between the photodetector and the light source.

In some embodiments, the head of the spectrophotometer includes a battery and a wireless communication interface.

In some embodiments, the head of the spectrophotometer occupies a volume of less than 10 cubic centimeters.

In some embodiments, the receiving fiber is a first receiving fiber, and the spectrophotometer further includes a second receiving fiber.

In some embodiments, the receiving fiber is a multimode fiber.

In some embodiments: the minimally invasive device is wearable device: the insertion tube is a hollow needle configured to penetrate the surface of the skin of a subject, the wearable device includes a housing, the head of the spectrophotometer is in the housing, and the hollow needle is secured to the housing.

In some embodiments, the housing is configured to be secured to the skin of the subject with an adhesive sheet.

In some embodiments, the minimally invasive device further includes an actuator for vibrating the hollow needle.

In some embodiments: the minimally invasive device is a biopsy needle, the insertion tube is a percutaneous needle of the biopsy needle, and the biopsy needle includes a handle.

In some embodiments, the head of the spectrophotometer is in the handle.

In some embodiments, the transmitting fiber and the receiving fiber are configured to be retracted to vacate a volume, for holding a biopsy sample, at the tip of the percutaneous needle.

In some embodiments, the head of the spectrophotometer is configured to slide within the handle to advance or retract the transmitting fiber and the receiving fiber within the percutaneous needle.

In some embodiments, each of the transmitting fiber and the receiving fiber has a bend within the handle, the bend being configured to include varying amounts of fiber and to enable the transmitting fiber and the receiving fiber to be advanced or retracted within the percutaneous needle.

In some embodiments, a portion of the transmitting fiber or a portion of the receiving fiber is embedded within the wall of the percutaneous needle.

In some embodiments: the minimally invasive device is an endoscope, the insertion tube is a shaft of the endoscope, and the endoscope includes a handle.

In some embodiments, the head of the spectrophotometer is in the handle. In some embodiments, a portion of the transmitting fiber or a portion of the receiving fiber is embedded within the wall of the shaft of the endoscope.

In some embodiments, the minimally invasive device further includes a treatment laser fiber, and a portion of the transmitting fiber or a portion of the receiving fiber is contained, with the treatment laser fiber, in a sheath.

According to an embodiment of the present disclosure, there is provided a method, including: obtaining spectrophotometric data from a subject with a system including a minimally invasive device and a spectrophotometer.

In some embodiments, the method further includes calibrating another sensor, on the subject, based on the spectrophotometric data.

In some embodiments, the method further includes calibrating the spectrophotometer based on another sensor on the subject.

In some embodiments, the method further includes: applying energy to a tissue of the subject, and estimating the temperature of the tissue based on the spectrophotometric data.

In some embodiments, the method further includes performing laser lithotripsy in a kidney of the subject, wherein the estimating of the temperature of the tissue includes estimating the temperature of kidney tissue of the subject.

In some embodiments, the estimating of the temperature includes estimating the center wavelength of an absorption peak of water.

According to an embodiment of the present disclosure, there is provided a system including: a minimally invasive device; and a spectrophotometer, the spectrophotometer including: a light source; and a photodetector, wherein: the spectrophotometer is in a channel of an insertion tube of the minimally invasive device, or the spectrophotometer is configured to be optically coupled to tissue of a subject through a channel of an insertion tube of the minimally invasive device.

BRIEF DESCRIPTION OF THE DRAWINGS

Features, aspects, and embodiments are described in conjunction with the attached drawings, in which:

FIG. 1B is a schematic illustration of a spectrophotometer head, according to an embodiment of the present disclosure;

FIG. 1C is a schematic illustration of a spectrophotometer head, according to an embodiment of the present disclosure;

FIG. 1D is a schematic illustration of a photodetector mounting arrangement, according to an embodiment of the present disclosure;

FIG. 1E is a schematic illustration of a spectrophotometer head, according to an embodiment of the present disclosure;

FIG. 1F is a schematic illustration of a photodetector mounting arrangement, according to an embodiment of the present disclosure;

FIG. 1G is a schematic illustration of a spectrophotometer head, according to an embodiment of the present disclosure;

FIG. 1H is a schematic illustration of a photodetector mounting arrangement, according to an embodiment of the present disclosure;

DETAILED DESCRIPTION

The detailed description set forth below in connection with the appended drawings is intended as a description of exemplary embodiments of a minimally invasive device with spectrophotometer provided in accordance with the present disclosure and is not intended to represent the only forms in which some embodiments may be constructed or utilized. The description sets forth the features of the present disclosure in connection with the illustrated embodiments. It is to be understood, however, that the same or equivalent functions and structures may be accomplished by different embodiments that are also intended to be encompassed within the scope of the disclosure. As denoted elsewhere herein, like element numbers are intended to indicate like elements or features.

Figure 1A:
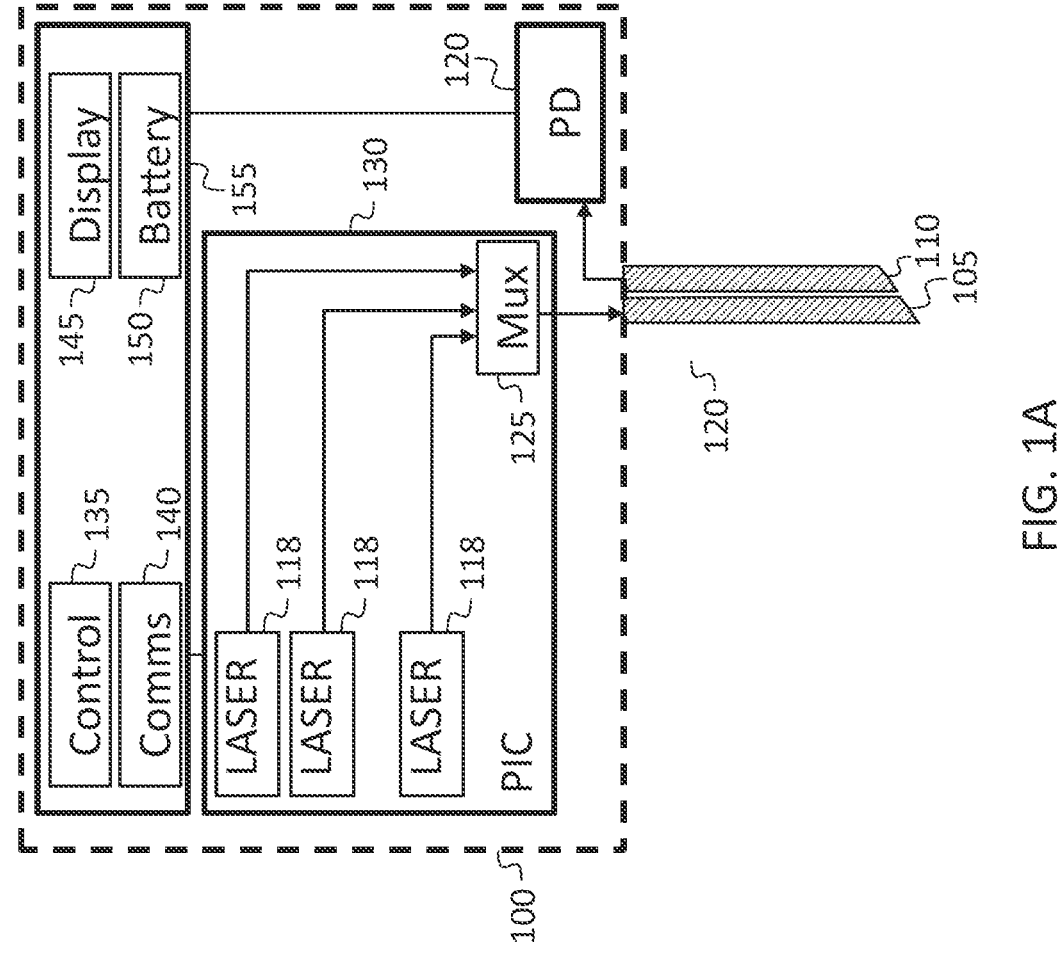
FIG. 1A is a block diagram of a spectrophotometer, according to an embodiment of the present disclosure.

In some embodiments, a spectrophotometer may be used with a minimally invasive device to obtain internal spectrophotometric data from a subject (e.g., a patient). A system for obtaining such data may include a spectrophotometer and a minimally invasive device. The spectrophotometer, illustrated, for one embodiment, in FIG. 1, may include a spectrophotometer head 100 and one or more fibers, e.g., one or more transmitting fibers 105 and one or more receiving fibers 110. The minimally invasive device may include an insertion tube (e.g., a percutaneous or subcutaneous needle, or any other tube configured to extend from the exterior of the subject to the interior of the subject). The fibers 105, 110 may extend from the spectrophotometer head, and into the subject, through a channel 115 (see, e.g., FIG. 4B) of the insertion tube of the minimally invasive device.

As shown in FIG. 1, the spectrophotometer head may include a plurality of lasers 118 (e.g., each operating at a different respective wavelength), for generating light to be transmitted through the transmitting fiber, and a photodetector 120 for detecting light received through the receiving fiber. The lasers may cover a wavelength range from 1.2 um to 2.5 um, or from 0.4 um to 1.2 um, or from a lower wavelength that is between 0.4 um and 2.5 um to an upper wavelength that is between 0.4 um and 2.5 um and greater than the lower wavelength. In operation, various wavelengths of probe light may be transmitted into the tissue of the subject through the transmitting fiber, and, at each wavelength, light received through the receiving fiber (after scattering within the tissue of the subject, or being transmitted through the tissue of the subject, or both) is measured. The photodetector 120 may be sensitive over the same ranges of wavelengths as those transmitted by the transmitting fiber.

In embodiments with several lasers, each laser may operate in a different respective wavelength range (although the wavelength ranges may overlap), and the outputs of the lasers may be combined using a multiplexer 125, which may be, e.g., an arrayed waveguide grating, an echelle grating, or a cascaded Mach-Zehnder multiplexer. The wavelength of the light transmitted through the transmitting fiber 105 may be varied by switching between different lasers, each operating at a different respective wavelength, or by tuning one or more lasers, or both (e.g., tuning each laser over a relatively narrow range, and switching to another laser when light outside the range of the currently operating laser is needed).

The photodetector may be a photodiode, e.g., an amplified photodiode (such as an avalanche photodiode). The detection of the received light may be incoherent, or "direct" detection, or it may be coherent detection (e.g., homodyne or heterodyne detection). In the case of homodyne or heterodyne detection, the receiving fiber 110 may be a single-mode fiber, and a portion of the probe light separated from the main probe beam using a splitter (or using a reflection—e.g., an internal reflection at the proximal end of the transmitting fiber) may be used as the local oscillator for the detector. In the case of incoherent detection, the receiving fiber 105 may be a multi-mode fiber, to increase the optical power collected. In some embodiments, a plurality of receiving fibers 110 is used (coupled to one or more shared photodetectors, or each coupled to a respective photodetector) to increase the magnitude of the signal corresponding to the received light.

The lasers 118 and the multiplexer 125 may be part of a photonic integrated circuit (PIC) 130. For example, the PIC 130 may be a silicon PIC, and the lasers may be mounted on the PIC 130 (e.g., flip-chip mounted in cavities in the PIC 130, and coupled to waveguides on the PIC 130). The multiplexer 125 may be fabricated on the PIC 130 (e.g., in the top surface of the PIC 130) and the photodetector 120 may be (i) fabricated in the top surface of the PIC 130 (e.g., it may be an integral part of the PIC 130), or (ii) mounted on the surface of the PIC 130, parallel to the PIC 130, and (1) configured to have light coupled to its exposed surface or (2) configured to have light edge-coupled to it, or (iii) mounted on the surface of the PIC 130, perpendicular to the PIC 130, and configured to have light coupled to its exposed surface. The proximal end of the transmitting fiber 105 may be secured in a V-groove in the PIC 130; the positioning of the transmitting fiber 105 in the V-groove may cause the proximal end of the transmitting fiber 105 to be aligned to a corresponding waveguide on the PIC 130.

The proximal end of the receiving fiber 105 may also be secured in a V-groove in the PIC 130. The proximal end facet of the receiving fiber 105 may abut against the photodetector 120, or it may be separated from the photodetector 120 by a small gap (which may be filled with an index-matching compound). If the photodetector 120 is configured to receive light propagating perpendicular to the plane of the PIC 130, the proximal end facet of the receiving fiber 110 may be polished at an angle such that light exits from the fiber (and illuminates the photodetector 120), after internal reflection from the angle-polished facet, in a direction perpendicular to the fiber. If the photodetector 120 is mounted on the surface of the PIC 130, perpendicular to the PIC 130, it may be secured to, and wire-bonded to, a ceramic substrate with wraparound metallization for forming connections from conductive traces on the PIC 130 and the photodetector 120 (through the wire bonds) (as discussed in further detail below).

FIGS. 1B-1H show laser and photodetector configurations, according to several different embodiments. In each of these embodiments, the transmitting fiber 105 is a single-mode fiber attached to a V-groove 162 on the PIC 130, which is mounted on a printed circuit board (PCB) 164. In the embodiment of FIG. 1B, the photodetector (PD) 120 is packaged separately in a TO can. The receiving fiber 110 may be a multimode fiber (MMF) coupled into the input window of the TO can. The leads of the TO can may turn 90 degrees, so that the receiving fiber 110 does not need to have a 90-degree bend. Light isolation (between the lasers of the laser diode array (LD array) and the photodetector 120) may be provided by the TO can.

In the embodiment of FIGS. 1C and 1D, a bare photodetector die 120 is mounted separately on the printed circuit board 164 and connected to the printed circuit board 164 with wire bonds 166. A 45-degree turning prism 168, which covers the active region of the photodetector 120, is used to change the direction of the light from the receiving fiber 110 so that it is incident on the surface of the photodetector 120. The hypotenuse of the turning prism 168 may be coated (e.g., with metal) to increase its reflectivity. An opaque enclosure 169 for light isolation may wrap around photodetector 120 to prevent leakage light from the transmitting side from reaching the photodetector 120.

In the embodiment of FIGS. 1E and 1F, a bare photodetector die 120 is mounted on the PIC 130 with a ceramic substrate 170. The photodetector die 120 and the ceramic substrate 170 are mounted perpendicular to the PIC 130, and no turning of the received light is needed. The receiving fiber 110 may be a multimode fiber (MMF) secured in a V-groove 162 on the PIC 130. The same V-groove 162 may have an opening or cavity for receiving the photodetector die 120 and the ceramic substrate 170, so that the receiving fiber 110 is self-aligned to the photodetector die 120. The substrate 170 may have wrap-around metal, so that connections may be made via two-sided wire bonding, as shown in FIG. 1F. One or more baffles 171 on the PIC 130 may provide light isolation.

In the embodiment of FIGS. 1G and 1H, a bare photodetector die 120 is integrated on the PIC 130 with a focusing lens 172. The receiving fiber 110 may be a multimode fiber (MMF) secured in a V-groove 162 on the PIC 130. The same V-groove 162 may have an opening or cavity for receiving the focusing lens 172, which focuses light into a multi-mode waveguide 174, on the PIC 130, between the focusing lens 172 and the photodetector die 120. The photodetector die 120 is edge-coupled to the waveguide. The bare photodetector die 120 is flip-chip bonded to the PIC 130. One or more baffles 171 on the PIC 130 may provide light isolation.

Referring again to FIG. 1A, the spectrophotometer head 100 may further include (i) a control circuit 135 (which may be (or include) a processing circuit, discussed in further detail below) for controlling the lasers and controlling the reading of the photodetector 120, (ii) a communication interface circuit 140 for exchanging data, status information, or control commands, through a wireless (e.g., Bluetooth) communication link or through a wired communication link, with one or more other devices (e.g., with a mobile phone carried by the subject, or with a piece of clinical equipment; from such a remote device, the data may be further analyzed or communicated to an electronic medical record (EMR)), (iii) a display 145 (e.g., for reporting measurements to the subject or to a clinician), and (iv) a battery 150. These components may be constructed on a printed circuit board which may be referred to as a control and RF communications board 155. In some embodiments, when a wireless communication link is employed, and a battery is used to power the spectrophotometer, the spectrophotometer may be wireless; in other embodiments wires may be used to supply power to the spectrophotometer or for communications with the spectrophotometer.

In part because a significant portion of the optical components of the spectrophotometer may be integrated into, or mounted on, the PIC 130, the entire spectrophotometer head 100 may occupy a small volume (e.g., a volume between 0.01 cubic centimeter and 1000.00 cubic centimeters, e.g., a volume less than 300 cubic centimeters or less than 10 cubic centimeters). In some embodiments, the spectrophotometer head 100 may have overall dimensions not exceeding 15 mm×15 mm×2.5 mm. In some embodiments the spectrophotometer is constructed to be sufficiently inexpensive to be used as a single use device. In such an embodiment, the transmitting and receiving fibers 105, 110 may be secured to the spectrophotometer without connectors (the presence of which would allow, for example, the spectrophotometer head 100 to be reused, with single-use fiber bundles). If the minimally invasive device is also configured to be a single-use device, the spectrophotometer may be integrated with the single use device (e.g., the spectrophotometer head 100 may be installed in a housing or handle of the minimally invasive device).

Figure 2A:
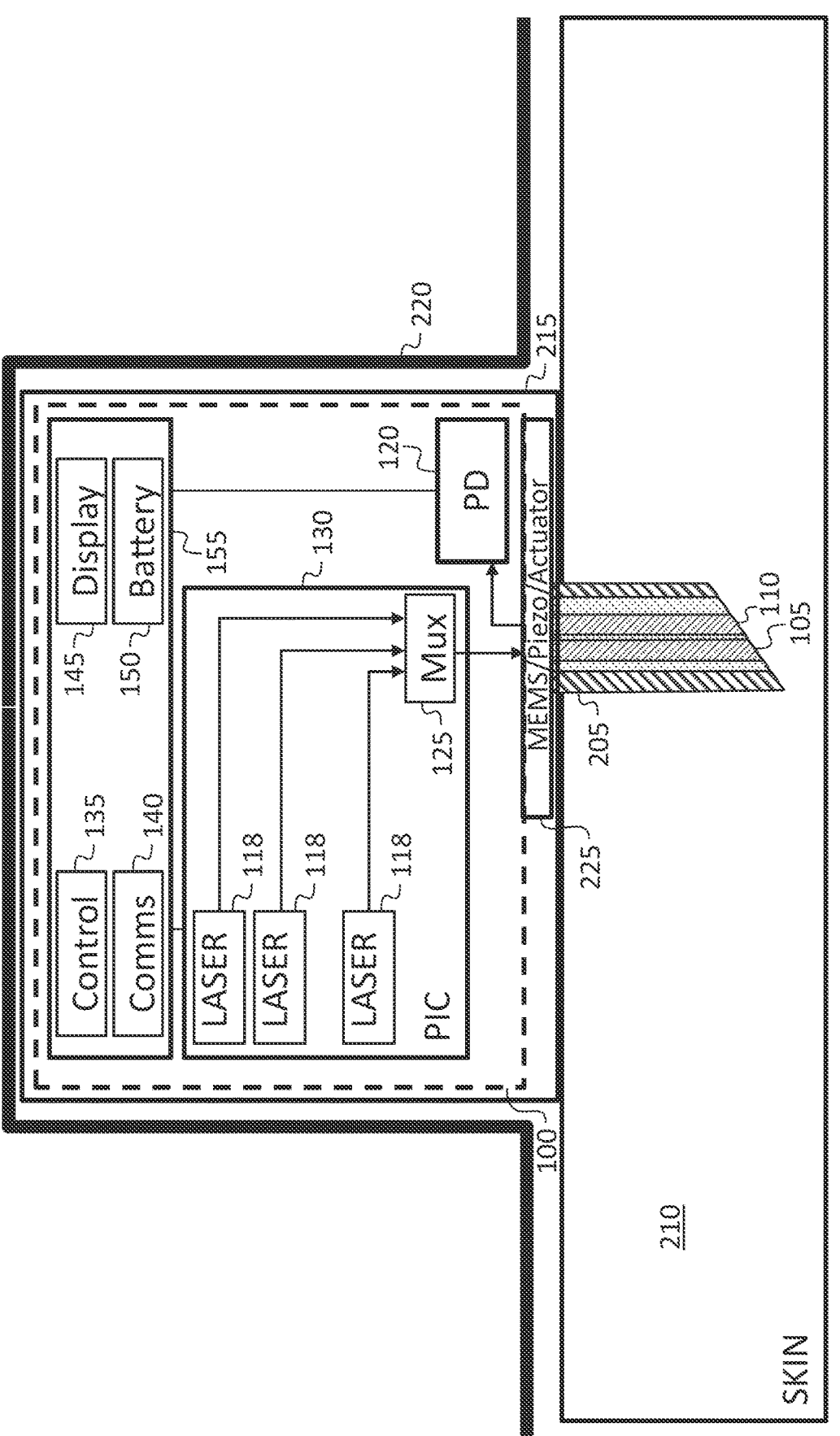
FIG. 2A is a schematic illustration of a spectrophotometer integrated into a minimally invasive device, according to an embodiment of the present disclosure.

The spectrophotometer may be assembled with, or used with, various minimally invasive devices, each of which may provide a path into the subject for one or more transmitting fibers 105 and one or more receiving fibers 110. For example, the minimally invasive device of FIG. 2A is a wearable patch-attached optical module which includes (i) a housing 215 (secured to the skin 210 with an adhesive sheet, e.g., an adhesive bandage 220) which may house the head 100 of the spectrophotometer, and, (ii) secured to the housing, an insertion tube, which may be a transcutaneous needle 205. As used herein, a "transcutaneous needle" is a percutaneous needle or a subcutaneous needle. The percutaneous needle 205 may puncture the skin 210 of the subject and may contain, within the lumen of the percutaneous needle 205, one or more transmitting or receiving optical fibers 105, 110.

The patch-attached optical module may compute a spectrum and measure analytes like glucose directly in the blood or interstitial fluid of the subject. The patch-attached optical module may provide continuous monitoring, data from which may be transmitted in real time or retrieved later and stored in EMR history. The transcutaneous needle (or "optical needle") may be applied to the body by the subject in a home setting. Real-time monitoring may be provided by the patch-attached optical module, and, in some embodiments, medical personnel may be automatically alerted when certain conditions are present. The spectrophotometer may perform monitoring of multiple analytes, such as glucose, water (to assess hydration), lactate, creatinine, and others. The patch-attached optical module may be battery powered with sufficient charge for one week of uninterrupted wearing. At the end of the (e.g., one-week) monitoring period (or when the battery is exhausted) the patch-attached optical module may be disposed of.

The optical module may adhere to the skin of the subject, and a length (e.g., of 1 mm-10 mm) of the transcutaneous needle (e.g., the portion of the needle protruding from the module) may be inserted into the dermis of the subject. In some embodiments the direction of insertion is not perpendicular to the surface of the subject's skin, so that the depth of the needle within the subject's body is less than the inserted length. In some embodiments, a MEMS (microelectromechanical system) module may occasionally (e.g., periodically or sporadically) vibrate the needle to shake off clotting, scabbing or a buildup of other substances that may accumulate on the tip of the transcutaneous needle. The MEMS module may include a piezoelectric or other type of mechanical actuator 225 to move the transcutaneous needle (e.g., in the axial direction, or in another direction). For example, a piezoelectric actuator in the lumen of the transcutaneous needle may, when driven, cause the needle to vibrate (as a rigid body, or in a bending mode) in a transverse direction. In some embodiments, the transcutaneous needle, which may have an outside diameter of about 0.5 mm (e.g., between 0.3 mm and 1.0 mm), contains optical fibers with diameters of approximately 200 microns.

The transcutaneous needle may include metal sheathing with the optical fiber cores inside the sheathing, or it may have plastic sheathing for added comfort and compliance; in some embodiments the exterior surface of the transcutaneous needle is coated with a coating for improving biocompatibility. The transcutaneous needle may have a non-uniform cross section for engineered flexibility (e.g., it may have a diameter that decreases with increasing distance from the patch-attached optical module) and it may have a non-circular (e.g., oval or elliptical) cross section. The patch-attached optical module may include several needles to enhance readings and prolong module viability. The transcutaneous needle may be a less invasive needle compared to an electrical needle that may be employed by an electrical needle sensor (e.g., the optical needle may extend to a smaller depth within the subject's body). In some embodiments, the patch-attached optical module operates as a transcutaneous fiber probe and broad spectral sensor in a wearable device. It may provide broadband spectral sensitivity, to quantify a variety of analytes (as contrasted with electrical probes, which may have limited analyte sensitivity), and it may provide direct optical access to blood to improve analyte recognition, relative to non-invasive optical systems.

Figure 2B:
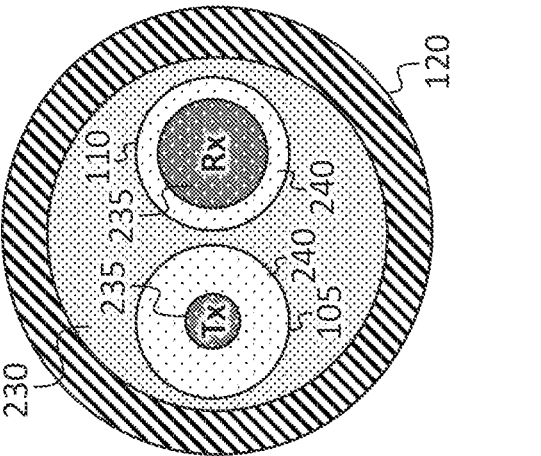
FIG. 2B is a cross sectional view of a portion of the embodiment of FIG. 2A.

FIG. 2B is a cross-sectional view of the transcutaneous needle 120. The channel, or "lumen", of the transcutaneous needle 120 may also include a fill material 230 (e.g., a dielectric material, such as an epoxy) for filling the gaps between the fibers and the inner surface of the wall of the transcutaneous needle 120, and for securing the fibers within the channel of the transcutaneous needle 120. Each fiber may be composed of glass or plastic and may include (e.g., consist of) a core 235 within a cladding 240, the cladding having a lower index of refraction than the core. FIG. 2B is not drawn to scale. As mentioned above, the transmitting fiber 105 may be a single-mode fiber with a relatively small core, and the receiving fiber 105 may be a multimode fiber with a larger core.

In some embodiments, a first sensor (e.g., the system of FIGS. 2A and 2B), may be used together with a second sensor, on the same subject, for calibration. Such calibrations may be done when the first sensor or the second sensor is initially placed on the subject (to calibrate for subject-to-subject physiological and anatomical variability), and periodically (or continuously) thereafter to calibrate for instrument drift, or physiological and anatomical changes of the subject.

In some embodiments, the first sensor and the second sensor both measure the same tissue site; this may improve the accuracy of the calibration and of any subsequently obtained calibrated measurements. For example, a second, non-invasive sensor may be integrated into the housing of the embodiment of FIG. 2A, along with the spectrophotometer shown in FIG. 2A; the second sensor may be a second, similar spectrophotometer, which obtains spectra noninvasively by illuminating the skin with a probe beam and measuring light that scatters back (after scattering within the subcutaneous tissue) into one or more photodetectors of the second spectrophotometer. The first sensor may be used for initial calibration of the second, or for occasional re-calibration of the second sensor. This configuration may improve the accuracy of the second sensor, enabling the user to gain more benefit from noninvasive measurements, and it may also improve the user experience by combining both sensors into one unit. In some embodiments a minimally invasive sensor (such as that of FIG. 2A) is used occasionally (e.g., daily or weekly) to calibrate a noninvasive sensor, which may be worn continuously by the subject. For example, in an embodiment in which both sensors are integrated into one housing, the invasive part is not or does not need to be permanently in place. It may be more convenient or comfortable for the user not to have it in place, and it may be retracted when not in use. In some embodiments the second sensor may be used to calibrate the first sensor (initially, or periodically or continuously). In some embodiment the two sensors (or more than two sensors) are jointly calibrated against each other (e.g., estimates of the quantity to be measured are generated after jointly estimating calibration parameters for both sensors).

In an embodiment with two sensors in which one of the sensors is used to calibrate the other, one (or both) of the sensors may measure invasively (e.g., using a needle (as in the embodiment of FIGS. 2A and 2B), wire, or biopsy device), or by pulling fluid through the skin surface, using reverse iontophoresis or magnetohydrodynamics. For re-calibration of one of the sensors, (i) analysis of that sensor's data may be used to determine when to re-calibrate, or (ii) re-calibration may be done on a time schedule, or (iii) the user may decide when to re-calibrate according to the user's convenience.

Various sensor measurement modalities may be used to calibrate a sensor like that of FIG. 2A, or an otherwise similar non-invasive spectrophotometer, for different biomarkers. For example, when the biomarkers to be measured are core body temperature, basal temperature, or skin temperature, the measurement modalities may include a thermistor or an infrared (IR) sensor on the surface of the skin or in a needle. When the biomarkers are total body hydration, skin hydration, or vascular volume, the measurement modalities may include a galvanic skin conductance sensor or an epidermal impedance sensor on the surface of the skin or in a needle. When the biomarkers are arterial blood glucose, venous blood glucose, capillary blood glucose, or interstitial glucose, the measurement modalities may include a lancet to draw blood coupled to an enzymatic colorimetric or electrochemical sensor, or a needle or wire to sample the interstitial fluid coupled to an enzymatic electrochemical sensor, or reverse iontophoresis or magnetohydrodynamics to draw the interstitial fluid to the surface of the skin, coupled to an enzymatic electrochemical sensor.

In some embodiments a spectrophotometer may be integrated with an instrument for image guided needle biopsy or resection. Such an instrument may be used in medicine to collect a sample of tissue from an area of interest to determine whether the tissue is healthy or not. Imaging techniques such as ultrasound, x-ray, CT, MRI, and mammography may be used in conjunction with disposable biopsy needles to help guide the sample collection process. The imaging allows the physician to simultaneously see the area of interest and the (disposable) needle tip. While imaging techniques have improved over time, challenges persist with making sure that the sample is being taken from the intended location and the occurrence rate of false negative diagnoses remains relatively high for certain conditions and anatomical locations. Collecting multiple samples can reduce the occurrence of false negatives but can increase the risk of injury to the surrounding tissue.

In some embodiments spectrophotometric data are obtained from the tissue, and a suitable spectroscopic technique (which may be selected based on, e.g., disease state or anatomical location), is employed to distinguish between healthy and diseased tissue. A needle configured to perform an optical spectrophotometric measurement (which may be referred to as an "optical biopsy needle" and which may be capable of performing a diagnostic measurement that is an alternative to a biopsy) or spectroscopically-assisted tissue resection device (such as an RF needle knife) with such a capability may significantly improve sample targeting by providing real time feedback to the physician.

Such a technique may be used to define a perimeter without the need to remove tissue for ex-vivo analysis. In a hybrid device, the needle configured to perform an optical spectrophotometric measurement is used in conjunction with a conventional needle design (physical sample removal) and the optical feedback is used to ensure the sample removal is from the intended location (optical fibers may be placed outside the core of the conventional needle, e.g., embedded in the walls of the insertion tube of the biopsy needle, as shown for example in FIG. 3D). In some embodiments, the spectrophotometer is sufficiently small and inexpensive to be a single use component, with the spectrophotometer head 100 integrated into the handle of a single-use biopsy needle.

Figure 3A:
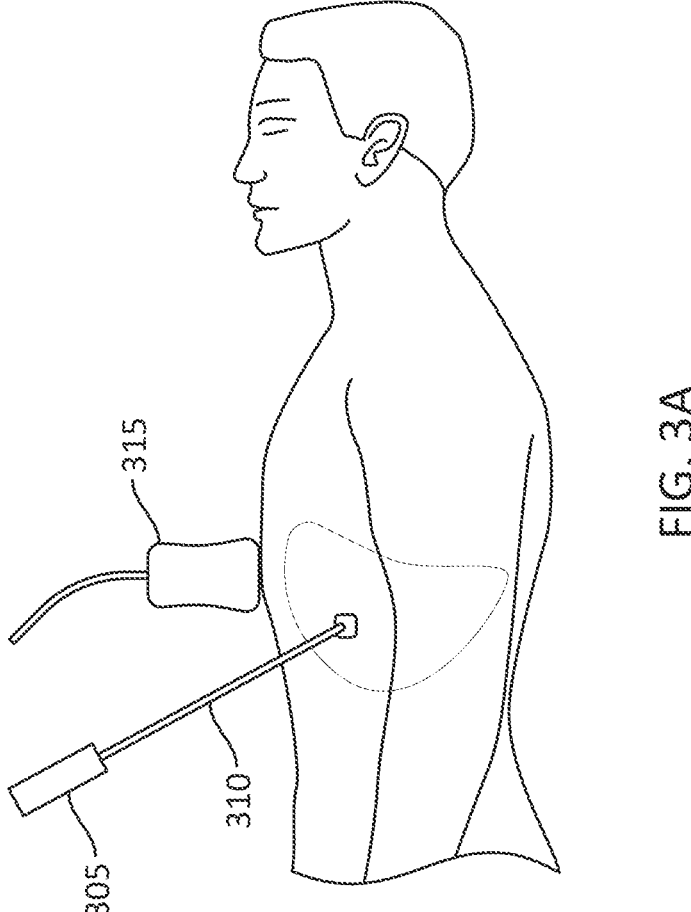
FIG. 3A is a schematic illustration of a spectrophotometer in use, according to an embodiment of the present disclosure.
Figure 3B:
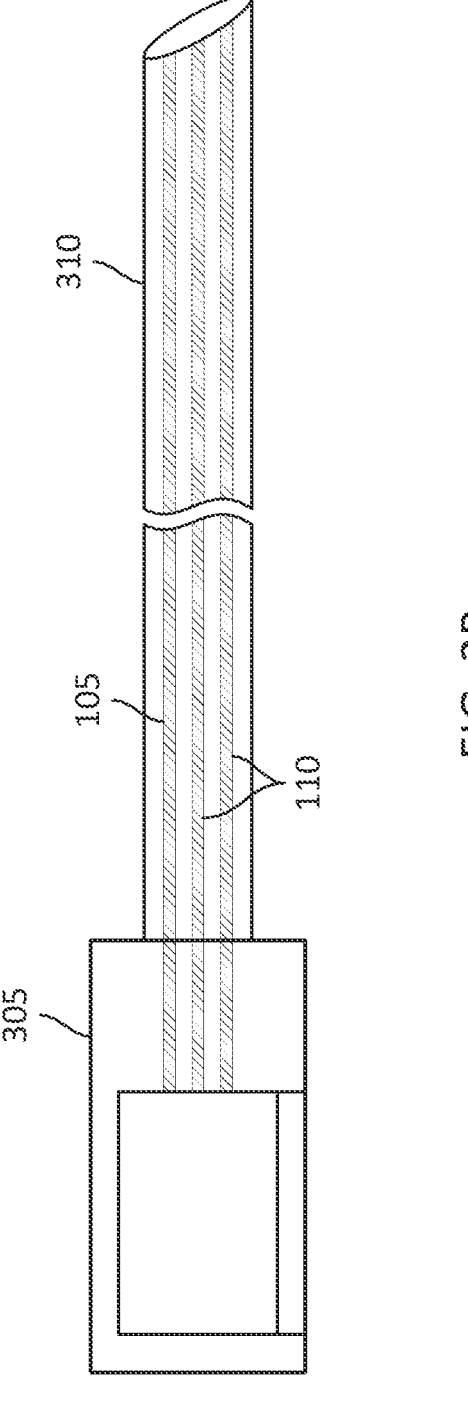
FIG. 3B is a schematic illustration of a spectrophotometer integrated into a minimally invasive device, according to an embodiment of the present disclosure.

FIG. 3A depicts an example use case for a percutaneous needle biopsy (of the liver in the example illustrated). A biopsy needle including a handle 305 and a percutaneous needle 310 is inserted into the tissue to be sampled. As shown in FIG. 3B, the spectrophotometer may be integrated into the biopsy needle, with the head 100 of the spectrophotometer being in the handle 305 of the biopsy needle, and the percutaneous needle 310 operating as the insertion tube through which the fibers 105, 110 extend into the interior of the subject. During the insertion and prior to the obtaining of the sample, (i) real-time data from the spectrophotometer (which may, for example, be used to distinguish between healthy and diseased tissue) and (ii) an ultrasonic imaging system (using an ultrasonic probe 315) may be used to guide the tip of the needle to the correct point in the subject.

Figures 3C, 3D:
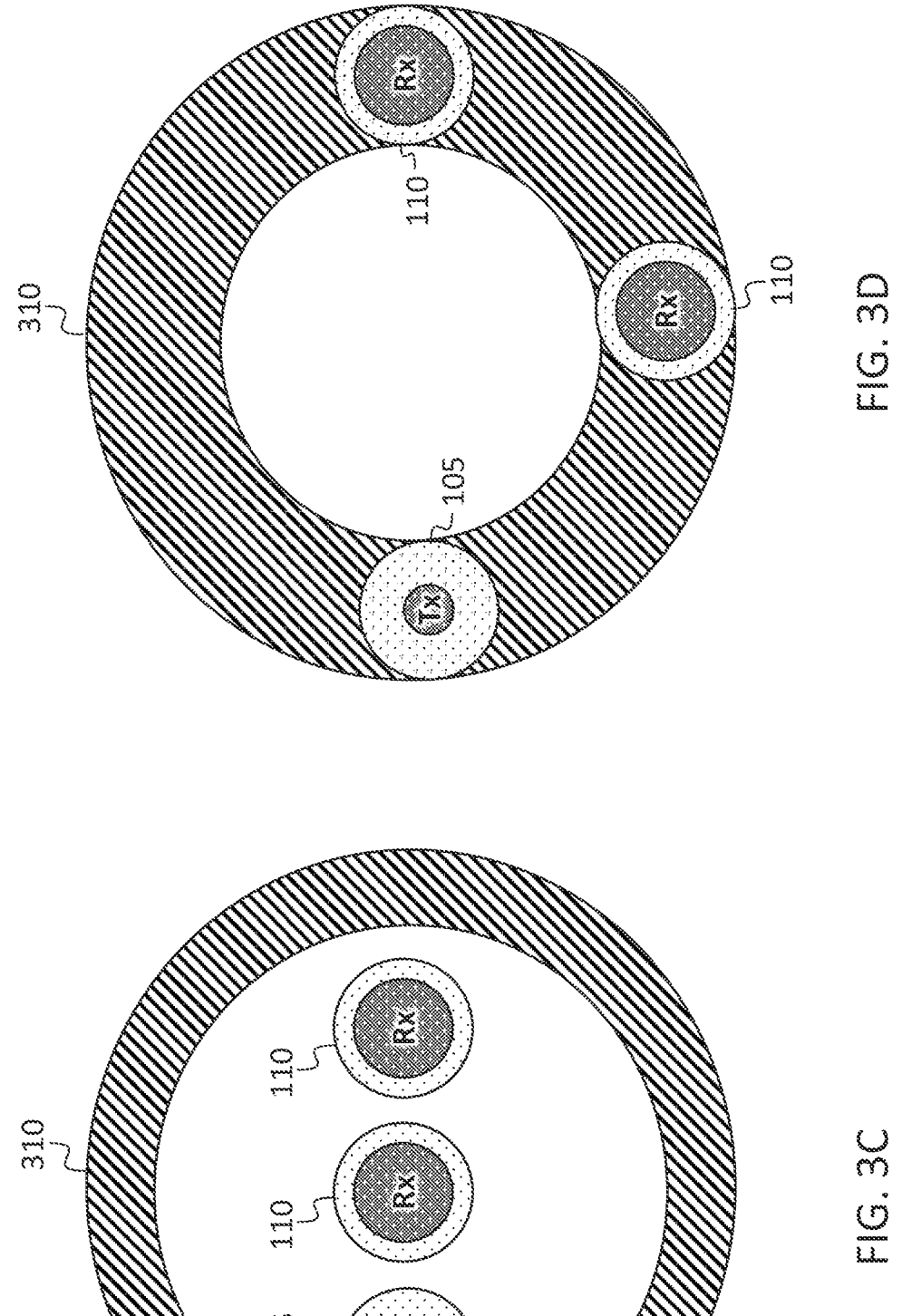
FIG. 3C is a cross sectional view of a portion of the embodiment of FIG. 3B, in one embodiment.
FIG. 3D is a cross sectional view of a portion of the embodiment of FIG. 3B, in another embodiment.

In some embodiments, the transmit fiber 105 and receive fibers 110 occupy the channel 115 inside the needle inner diameter, as illustrated in FIG. 3C, and the needle operates as a spectrophotometric inspection needle. In some embodiments the fibers are retracted part-way into the needle 310 and the volume at the tip of the needle that is vacated as a result is used to obtain a biopsy sample. In such an embodiment, a fiber loop or bend within the handle 305 of the biopsy needle may be (i) expanded to accommodate the additional fiber in the handle when the fibers 105, 110 are retracted into the needle, or (ii) contracted to supply additional fiber when the fibers 105, 110 are advanced to extend to the tip (or beyond the tip) of the needle 310. In other embodiments the spectrophotometer head 100 is configured to slide within the handle 305 of the biopsy needle to accommodate fiber from, or to supply fiber to, the percutaneous needle 310. In some embodiments the transmit and receive optical fibers are located outside the needle inner diameter, e.g., embedded into the wall of the percutaneous needle 310, as illustrated in FIG. 3D. In such an embodiment, the wall thickness of the percutaneous needle may be increased if needed to maintain adequate mechanical strength. The embodiment of FIG. 3D is a hybrid arrangement which combines a needle configured to perform an optical spectrophotometric measurement with a conventional biopsy needle. Such an embodiment may provide the physician with real time confirmation that the physical sample is being collected from the intended location.

In some embodiments, the minimally invasive device with which the spectrophotometer may be used is an endoscope. Diagnostic and therapeutic endoscopy may be employed to investigate and diagnose conditions in, for example, (i) the upper gastrointestinal tract (in a procedure that may be referred to as an esophagogastroduodenoscopy (EGD)), (ii) the liver, gallbladder, bile ducts, or pancreas (in a procedure that may be referred to as an endoscopic retrograde cholangiopancreatography (ERCP)), (iii) the colon (in a procedure that may be referred to as a colonoscopy), (iv) the lungs (in a procedure that may be referred to as a bronchoscopy), or (v) the urinary system (in a procedure that may be referred to as a ureteroscopy). While performing endoscopic procedures, a physicians may encounter features in the anatomy such as polyps or other growths. It may be difficult to determine if further action is required (such as taking a biopsy or removing suspect tissue). In some embodiments, a suitable spectroscopic technique is employed to distinguish between healthy, pre-cancerous, and cancerous tissue, and, in such an embodiment, endoscopic spectroscopy may have wide-ranging application in optical diagnostic techniques that may be employed instead of biopsies, for example, to discriminate between neoplastic and non-neoplastic polyps, to detect flat dysplasia in Barrett's esophagus, or to perform optical detection of field carcinogenesis.

Laser lithotripsy is a technique that may be used to treat kidney stones. A urologists may use a ureteroscope (a customized endoscope for use in the urinary system) to gain access to the urinary system, and laser light from a therapeutic laser, or "treatment laser" may be delivered to the target sites via an optical fiber that is passed through the working channel of the ureteroscope. Single-use disposable ureteroscopes and single-use laser delivery fibers may be employed for such procedures. Stones can be present in the bladder, ureter, or the kidney. The delivery of laser energy causes a localized increase in temperature. Elevated temperatures are a concern especially when treating stones that are present in the kidney as local temperatures above 60° C. may lead to irreversible cellular damage. In some embodiments, a spectrophotometer may offer the ability to reliably measure local temperatures inside the kidney, allowing the physician to check the temperature periodically and adjust the laser settings or irrigation flow as necessary.

Figure 4A:
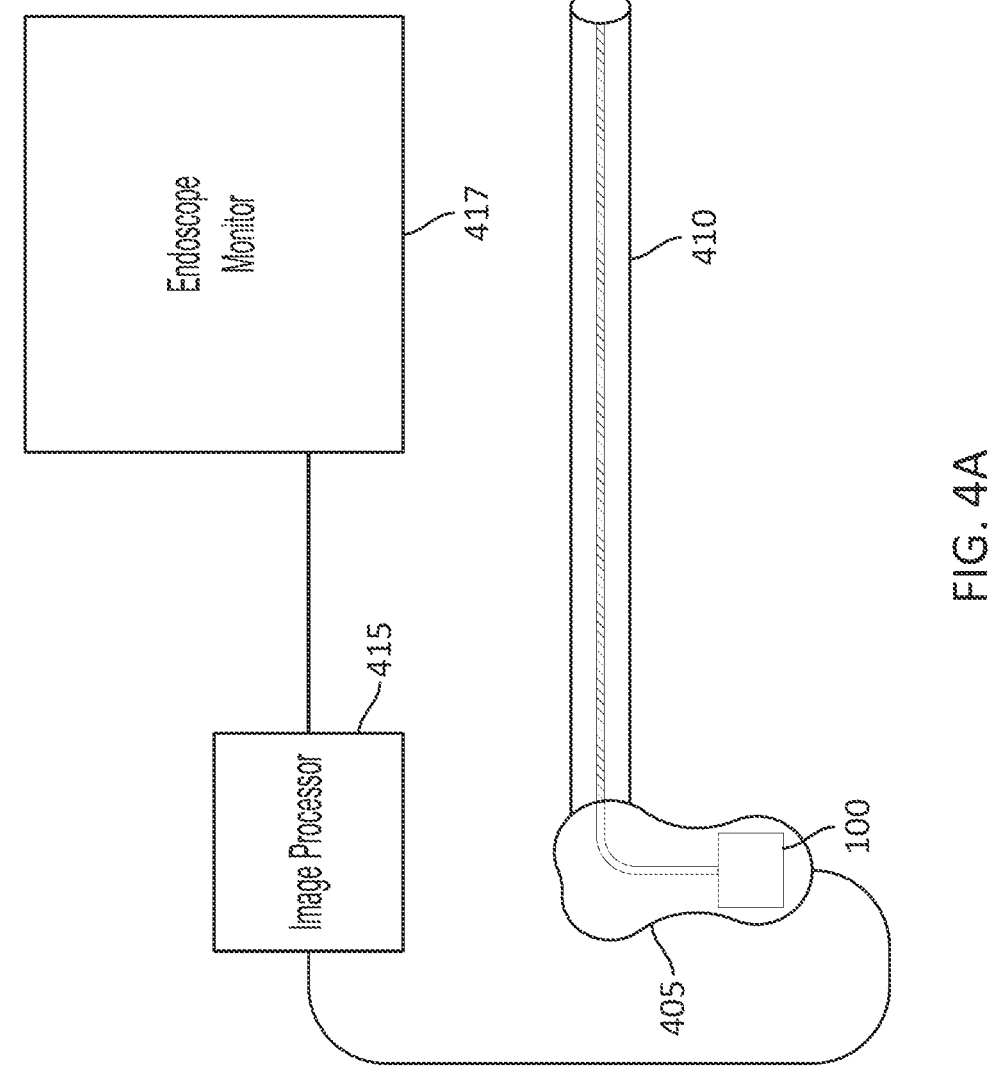
FIG. 4A is a schematic illustration of a spectrophotometer integrated into a minimally invasive device, according to an embodiment of the present disclosure.
Figure 4B:
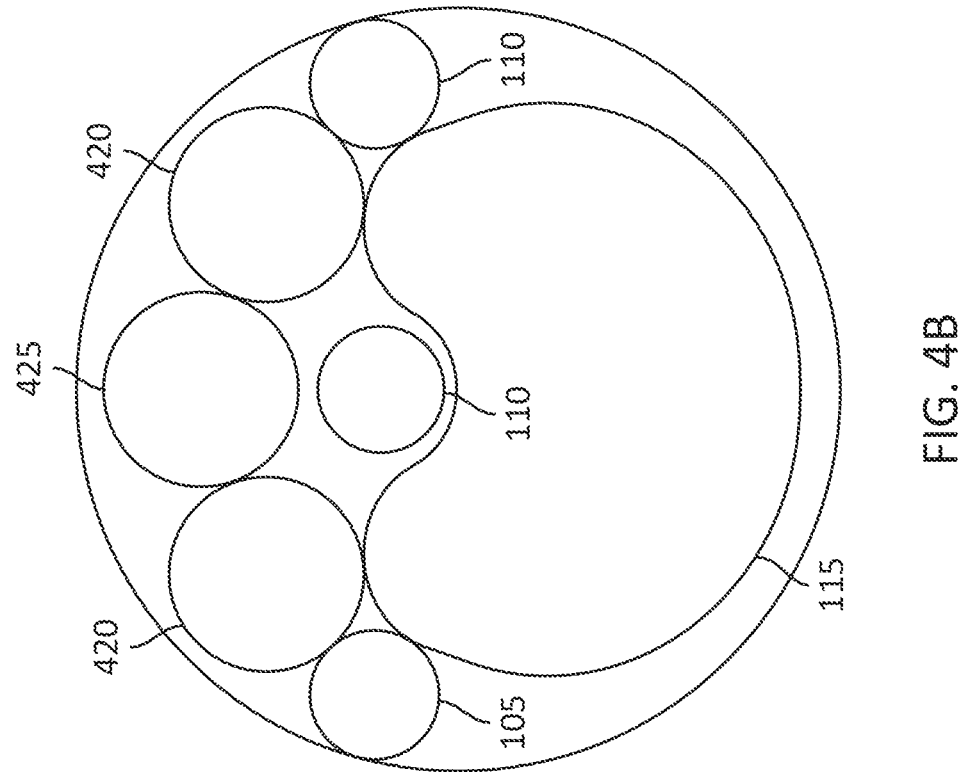
FIG. 4B is a cross sectional view of a portion of the embodiment of FIG. 4A.

FIG. 4A depicts a single-use endoscope set-up, which may be used for laser lithotripsy or other endoscopic procedures. The minimally invasive device (the endoscope) includes a handle 405 and a shaft 410, which operates as the insertion tube of the minimally invasive device. The endoscope is connected to an image processor 415, which is connected to an endoscopic monitor 417. The spectrophotometer head 100 may be integrated into the handle 405 of the endoscope, so that the entire device, including the endoscope and the spectrophotometer it contains, form a single-use device. FIG. 4B shows a cross-sectional image of the tip of the shaft. In the wall of the shaft 410 are embedded two light source cables 420 and one camera cable 425 (each of which may be an electrical cable; the camera and light source may be located at the distal end of the shaft 410). Also embedded in the wall of the shaft 410 (which may have a thicker portion as shown, to accommodate the embedded elements) are one or more transmitting fibers 105 and one or more receiving fibers 110 (one transmitting fiber 105 and two receiving fibers 110 in the embodiment of FIG. 4B) for the spectrophotometer. In operation, the physician may point the scope tip at an area of interest to perform a spectroscopic (e.g., spectrophotometric) analysis. The data resulting from the analysis may be transmitted wirelessly or through a wired connection and may be displayed on the endoscopic monitor or on a separate display; the data may also be sent to the electronic medical record system. If the endoscope is used for laser lithotripsy in the kidney, the treatment laser fiber may extend into the kidney through the channel 115, and the physician may, when a temperature reading is needed, retract the treatment laser fiber within the working channel 115 (so that the treatment laser fiber does not block the light from the transmitting fiber 105 and returning to the receiving fibers 110) and point the scope tip at the area of interest to complete a local temperature measurement. Temperature may be measured, for example, by measuring the center wavelength of the water absorption peak which occurs near 1400 nm, the wavelength of which is temperature dependent. For example, the spectrophotometer may (i) emit probe light at a number of wavelengths near 1400 nm, (ii) fit the intensity, as a function of wavelength, of the light returning through the receiving fibers 105, (iii) estimate the center wavelength of the absorption peak, and (iv) calculate (or look up, in a table) the corresponding temperature. The treatment laser fiber may include an optical fiber (including a core 235 and a cladding 240, and having a diameter of about 270 microns, suitable for use with a Nd:YAG treatment laser) within a sheath 440, as illustrated in FIG. 4C.

Figure 4D:
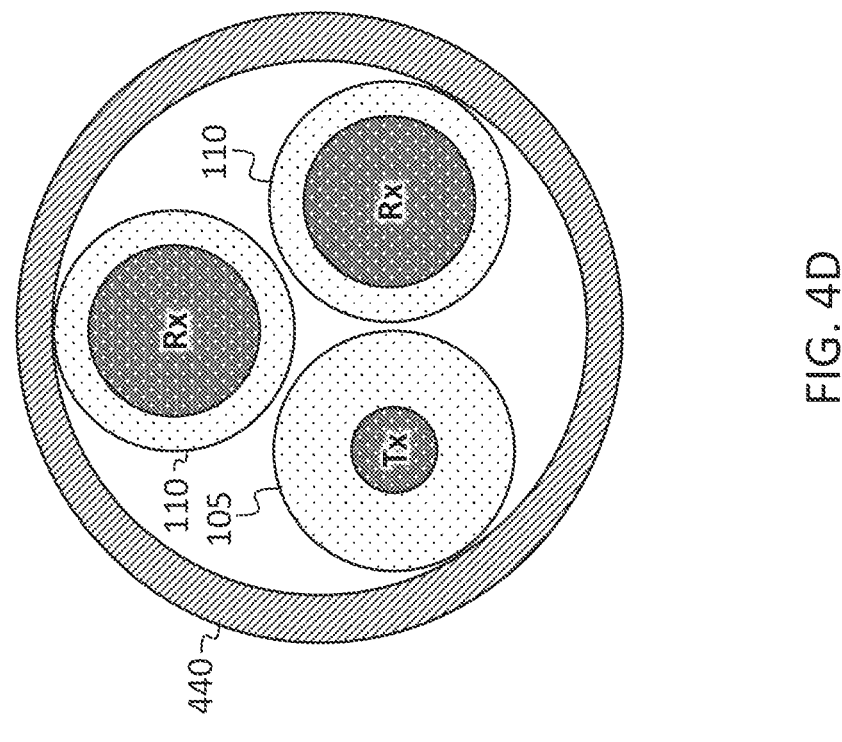
FIG. 4D is a cross sectional view of a fiber bundle, according to an embodiment of the present disclosure.
Figure 4C:
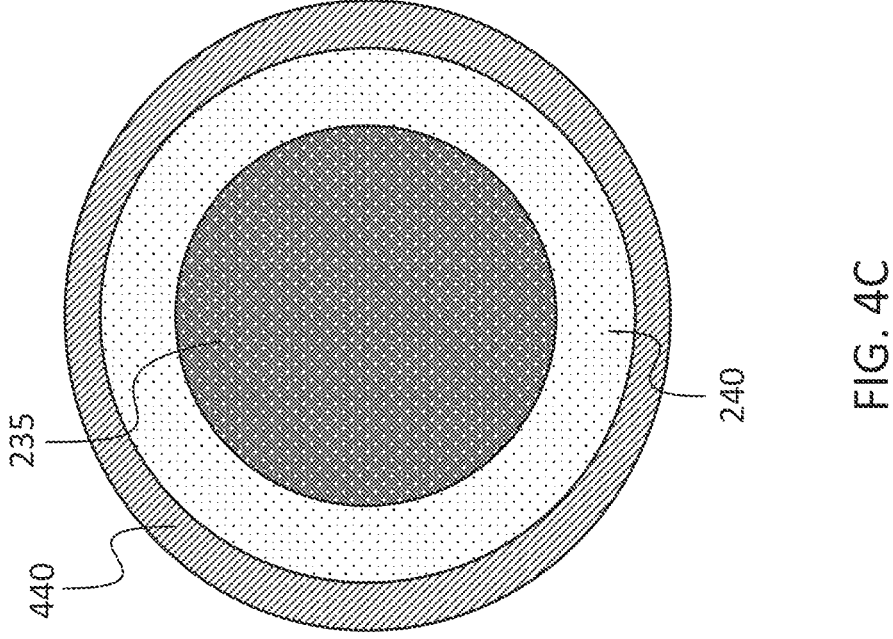
FIG. 4C is a cross sectional view of a treatment laser fiber, according to an embodiment of the present disclosure.

FIG. 4D shows a cross section of a fiber bundle including one transmitting fiber 105 and two receiving fibers 110, enclosed in a sheath 440, that may be part of a spectrophotometer (and that may be connected, at the proximal end, to the spectrophotometer head 100). The fiber bundle may be inserted through the channel of an endoscope, or of a stand-alone optical fiber biopsy catheter, or of a trocar, to be used (e.g., used exclusively) for minimally invasive spectroscopic sensing. When used with an endoscope, the spectrophotometer head 100 may be housed in the endoscope handle. The number and size of the fibers in the fiber bundle may be adjusted in a variety of arrangements. In such an embodiment, the fiber bundle may be extended beyond the tip of the endoscope to permit measurements to be taken in smaller, less accessible, locations. For example, the fiber bundle of FIG. 4D may be extended out of the distal end of the working channel of a bronchoscope, to make possible the collection of spectrophotometric data from within a lumen that is too narrow to accommodate the shaft of the bronchoscope.

Figures 5A, 5B:
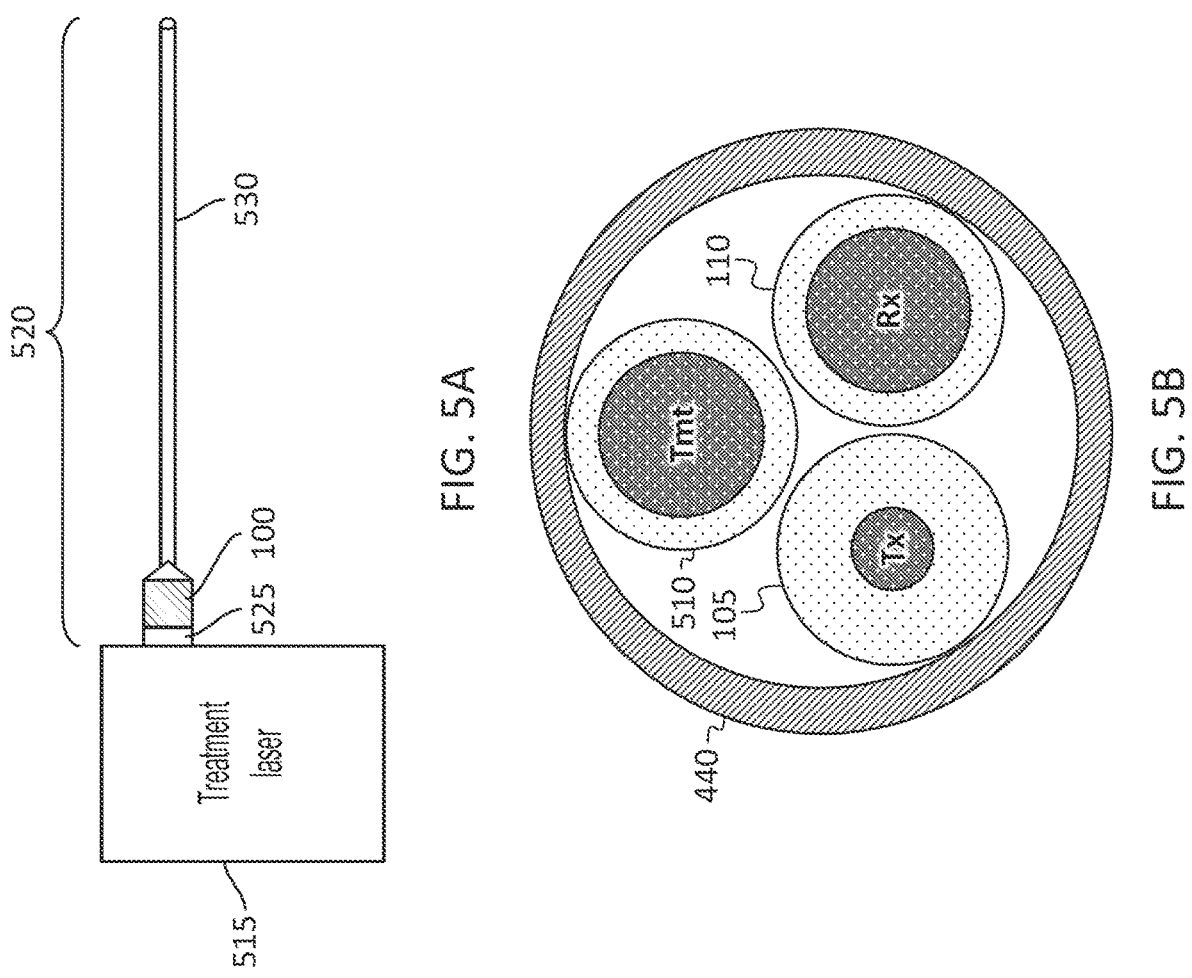
FIG. 5A is a schematic illustration of a treatment laser and a single-use spectrophotometer and treatment laser fiber assembly, according to an embodiment of the present disclosure.
FIG. 5B is a cross sectional view of a fiber bundle, according to an embodiment of the present disclosure.

In another embodiment, illustrated in FIGS. 5A and 5B, the treatment laser fiber 510 may be a smaller diameter fiber (e.g., 50 microns) and the treatment laser 515 may be a reusable fiber laser, capable of coupling sufficient optical power into a fiber of this diameter. The spectrophotometer may be part of a single-use spectrophotometer and treatment laser fiber assembly 520. The spectrophotometer and treatment laser fiber assembly 520 may include, at its proximal end, a connector for connecting it to the treatment laser 515, and, integrated with the connector 525, the spectrophotometer head 100. For example, a housing at the proximal end may contain the spectrophotometer head 100, and the connector 525 may be secured to the housing. The spectrophotometer and treatment laser fiber assembly 520 may also include a fiber shaft 530. In the fiber shaft 530, one or more transmitting fibers 105 and one or more receiving fibers 110 may be bundled, in a shared sheath 440, with the laser treatment fiber 510; a cross-sectional view of a fiber shaft 530 in such a configuration is shown in FIG. 5B. In operation, the fiber shaft may be inserted through the working channel of a ureteroscope. This arrangement may allow real-time temperature feedback to the physician during the laser lithotripsy procedure. This arrangement may also allow for other spectrophotometric measurements to be taken, including determination of stone composition or differentiation of healthy versus diseased tissue in the urinary system.

Figure 6:
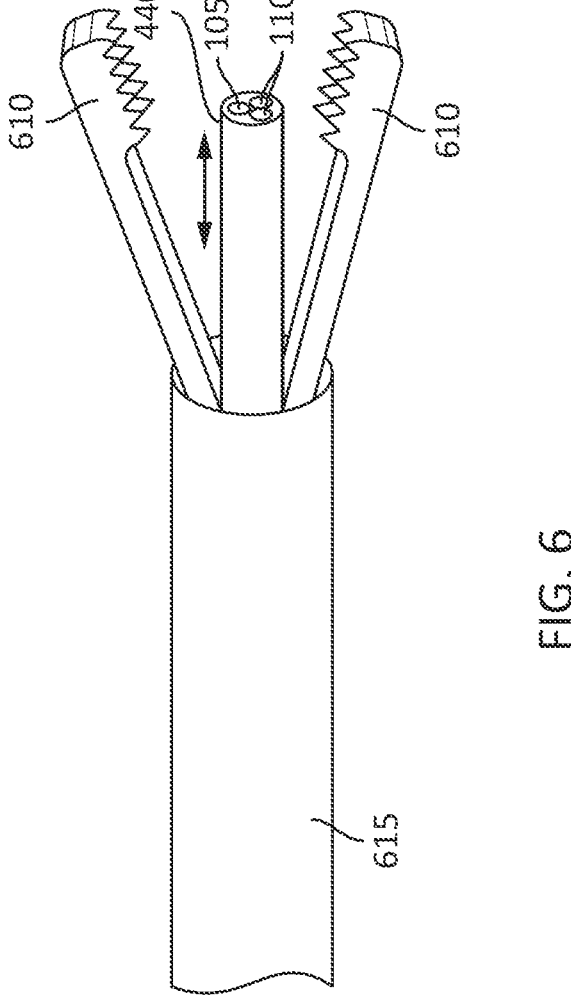
FIG. 6 is a schematic illustration of the distal end of biopsy forceps with a fiber bundle, according to an embodiment of the present disclosure.

In the embodiment of FIG. 6, the minimally invasive device is a pair of endoscopic biopsy forceps. The spectrophotometer head 100 may be integrated into the handle of the biopsy forceps, and the one or more transmitting fibers 105 and one or more receiving fibers 110 (enclosed in a suitable sheath 440) may extend through the interior of the shaft 615 of the biopsy forces to the distal end as shown. The fibers may be capable of being displaced longitudinally within the shaft, so that in operation, the fibers may be extended to obtain spectroscopic data from tissue, and then retracted so that the jaws 610 may be closed to obtain a sample. This method may allow a physician to increase the confidence level that the sample being acquired is from an area of specific interest.

Figure 7A:
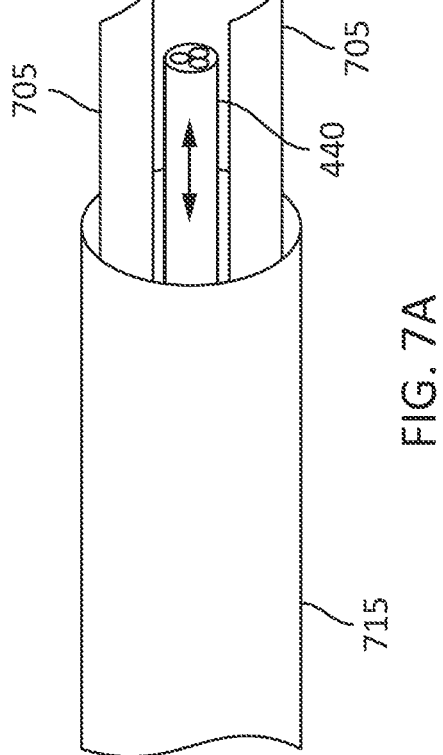
FIG. 7A is a schematic illustration of the distal end of a resection tool.
Figure 7B:
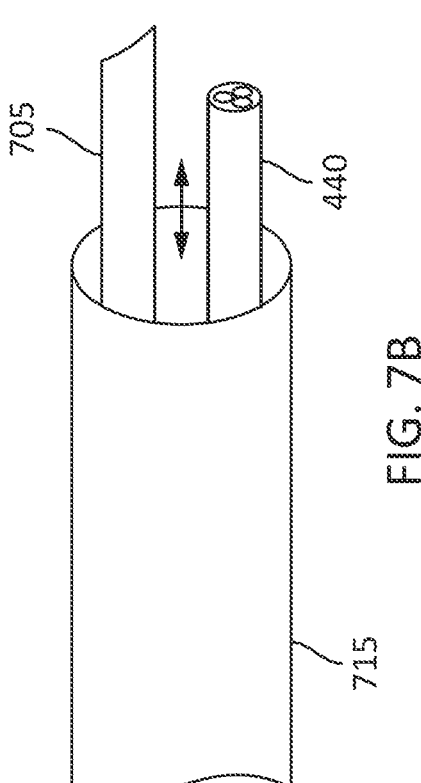
FIG. 7B is a schematic illustration of the distal end of a resection tool.

As mentioned above, in some embodiments a spectrophotometer may be integrated with a resection tool. The resection tool may be similar to biopsy forceps except it may be used for tissue cutting (e.g. cutting out a tumor or similar) rather than taking a sample for biopsy. In operation, high frequency (e.g., radio frequency (RF)) alternating electrical current is passed through tissue generating heat. FIG. 7A shows the distal end of the shaft 715 of a resection tool that includes a spectrophotometer. The resection tool shown is a bipolar resection tool having two electrodes 705; the electric current passes between the two electrodes 705. A fiber bundle including, e.g., one transmitting fiber 105 and two receiving fibers 110, enclosed in a sheath 440, extends to the distal end of the shaft and may be used to perform spectrophotometric analysis of tissue and identify the resection site. The fiber bundle may be secured within the shaft or it may be able to slide longitudinally (i.e., proximally and distally) within the shaft so that it may be extended or retracted. FIG. 7B shows a monopolar device, in which there is one active electrode at the device tip and a return electrode (also referred to as a "dispersive pad" or "grounding pad") is placed somewhere else in contact with the subject's body.

In some embodiments, the spectrophotometer does not include fibers and the light transmitted and received by the spectrophotometer head 100 is optically coupled through free space directly to the tissue. This may be accomplished, for example, by using a spectrophotometer head 100 that is sufficiently small to fit within the channel of the minimally invasive device (e.g., within the lumen of a needle that is part of the minimally invasive device) or by coupling the light through free space into a hollow core needle of the minimally invasive device, and utilizing wave guiding within the needle itself to deliver and receive light.

As used herein, a "photonic integrated circuit" is a component fabricated from a semiconductor wafer (e.g., from a silicon wafer or from a silicon-on-insulator wafer) that includes, on its surface, one or more optical waveguides, and that may include one or more other structures, mounted on, or fabricated on, the surface, including passive components such as couplers, and active components such as lasers or photodetectors. As used herein, a "minimally invasive device" is a device that provides access to the interior of a subject through an insertion tube, which is a tube with a diameter of at most 2 inches, that, in operation, extends from outside the subject into the subject. As used herein, an "insertion tube" includes, for example, the shaft of an endoscope, the cannula of a trocar, or the percutaneous needle of a biopsy needle or of a patch-attached optical module.

As used herein, "a portion of" something means "at least some of" the thing, and as such may mean less than all of, or all of, the thing. As such, "a portion of" a thing includes the entire thing as a special case, i.e., the entire thing is an example of a portion of the thing. As used herein, when a second quantity is "within Y" of a first quantity X, it means that the second quantity is at least X-Y and the second quantity is at most X+Y. As used herein, when a second number is "within Y %" of a first number, it means that the second number is at least $(1-Y/100)$ times the first number and the second number is at most $(1+Y/100)$ times the first number. As used herein, the word "or" is inclusive, so that, for example, "A or B" means any one of (i) A, (ii) B, and (iii) A and B.

The term "processing circuit" is used herein to mean any combination of hardware, firmware, and software, employed to process data or digital signals. Processing circuit hardware may include, for example, application specific integrated circuits (ASICs), general purpose or special purpose central processing units (CPUs), digital signal processors (DSPs), graphics processing units (GPUs), and programmable logic devices such as field programmable gate arrays (FPGAs). In a processing circuit, as used herein, each function is performed either by hardware configured, i.e., hard-wired, to perform that function, or by more general-purpose hardware, such as a CPU, configured to execute instructions stored in a non-transitory storage medium. A processing circuit may be fabricated on a single printed circuit board (PCB) or distributed over several interconnected PCBs. A processing circuit may contain other processing circuits; for example, a processing circuit may include two processing circuits, an FPGA and a CPU, interconnected on a PCB.

As used herein, when a method (e.g., an adjustment) or a first quantity (e.g., a first variable) is referred to as being "based on" a second quantity (e.g., a second variable) it means that the second quantity is an input to the method or influences the first quantity, e.g., the second quantity may be an input (e.g., the only input, or one of several inputs) to a function that calculates the first quantity, or the first quantity may be equal to the second quantity, or the first quantity may be the same as (e.g., stored at the same location or locations in memory as) the second quantity.

It will be understood that when an element or layer is referred to as being "on", "connected to", "coupled to", or "adjacent to" another element or layer, it may be directly on, connected to, coupled to, or adjacent to the other element or layer, or one or more intervening elements or layers may be present. In contrast, when an element or layer is referred to as being "directly on", "directly connected to", "directly coupled to", or "immediately adjacent to" another element or layer, there are no intervening elements or layers present.

Any numerical range recited herein is intended to include all sub-ranges of the same numerical precision subsumed within the recited range. For example, a range of "1.0 to 10.0" or "between 1.0 and 10.0" is intended to include all subranges between (and including) the recited minimum value of 1.0 and the recited maximum value of 10.0, that is, having a minimum value equal to or greater than 1.0 and a maximum value equal to or less than 10.0, such as, for example, 2.4 to 7.6. Similarly, a range described as "within 35% of 10" is intended to include all subranges between (and including) the recited minimum value of 6.5 (i.e., (1−35/100) times 10) and the recited maximum value of 13.5 (i.e., (1+35/100) times 10), that is, having a minimum value equal to or greater than 6.5 and a maximum value equal to or less than 13.5, such as, for example, 7.4 to 10.6. Any maximum numerical limitation recited herein is intended to include all lower numerical limitations subsumed therein and any minimum numerical limitation recited in this specification is intended to include all higher numerical limitations subsumed therein.

Although limited embodiments of a minimally invasive device with spectrophotometer have been specifically described and illustrated herein, many modifications and variations will be apparent to those skilled in the art. Accordingly, it is to be understood that a minimally invasive device with spectrophotometer employed according to principles of this disclosure may be embodied other than as specifically described herein. Features of some embodiments are also defined in the following claims, and equivalents thereof.

What is claimed is:

1. A system comprising:
a minimally invasive device; and
a spectrophotometer,
the spectrophotometer comprising:
    a transmitting fiber;
    a receiving fiber; and
    a head,
the head of the spectrophotometer comprising:
    a light source connected to the transmitting fiber; and
    a photodetector connected to the receiving fiber,
    wherein:
        a portion of the transmitting fiber is in an insertion tube of the minimally invasive device;
        a portion of the receiving fiber is in the insertion tube of the minimally invasive device; and
        the head of the spectrophotometer occupies a volume of less than 300 cubic centimeters.

2. The system of claim 1, wherein the minimally invasive device is a single-use device, and the spectrophotometer is integrated into the minimally invasive device.

3. The system of claim 1, wherein the head of the spectrophotometer comprises:
a plurality of lasers, each configured to operate within a different respective wavelength range, and
a multiplexer, having a plurality of inputs and an output, for combining the outputs of the lasers,
wherein:
    the transmitting fiber is connected to the output of the multiplexer,
    the head of the spectrophotometer comprises a photonic integrated circuit comprising the multiplexer
    the plurality of lasers is mounted on the photonic integrated circuit,
    each of the lasers is coupled into a waveguide on the photonic integrated circuit, and
    a proximal end of the transmitting fiber is secured in a V-groove on the photonic integrated circuit.

4. The system of claim 3, wherein:
the photodetector is mounted on a ceramic substrate,
the photodetector and the ceramic substrate are mounted on the photonic integrated circuit,
the photodetector is perpendicular to the photonic integrated circuit, and
the receiving fiber is secured in a V-groove in the photonic integrated circuit.

5. The system of claim 3, wherein:
the photodetector is mounted on the photonic integrated circuit and edge-coupled to a waveguide on the photonic integrated circuit,
the receiving fiber is secured in a V-groove in the photonic integrated circuit, and coupled to the waveguide, and
the multiplexer is an arrayed waveguide grating, an echelle grating, or a cascaded Mach-Zehnder multiplexer.

6. The system of claim 1, wherein the spectrophotometer is configured to perform coherent detection of light received via the receiving fiber.

7. The system of claim 1, wherein the head of the spectrophotometer occupies a volume of less than 10 cubic centimeters.

8. The system of claim 1, wherein the receiving fiber is a first receiving fiber, and the spectrophotometer further comprises a second receiving fiber.

9. The system of claim 1, wherein the receiving fiber is a multimode fiber.

10. The system of claim 1, wherein:
the minimally invasive device is wearable device:
the insertion tube is a hollow needle configured to penetrate the surface of the skin of a subject,
the wearable device comprises a housing,
the head of the spectrophotometer is in the housing, and
the hollow needle is secured to the housing.

11. The system of claim 10, wherein the minimally invasive device further comprises an actuator for vibrating the hollow needle.

12. The system of claim 1, wherein:
the minimally invasive device is a biopsy needle,
the insertion tube is a percutaneous needle of the biopsy needle, and
the biopsy needle comprises a handle.

13. The system of claim 12, wherein the head of the spectrophotometer is in the handle.

14. The system of claim 12, wherein the transmitting fiber and the receiving fiber are configured to be retracted to vacate a volume, for holding a biopsy sample, at the tip of the percutaneous needle.

15. The system of claim 12, wherein a portion of the transmitting fiber or a portion of the receiving fiber is embedded within the wall of the percutaneous needle.

16. The system of claim 1, wherein:

the minimally invasive device is an endoscope, the insertion tube is a shaft of the endoscope, and the endoscope comprises a handle.

17. The system of claim 16, wherein the head of the spectrophotometer is in the handle.

18. The system of claim 16, wherein a portion of the transmitting fiber or a portion of the receiving fiber is embedded within the wall of the shaft of the endoscope.

19. The system of claim 16, wherein the minimally invasive device further comprises a treatment laser fiber, and a portion of the transmitting fiber or a portion of the receiving fiber is contained, with the treatment laser fiber, in a sheath.

* * * * *